(12) United States Patent
Lee et al.

(10) Patent No.: US 10,671,893 B2
(45) Date of Patent: Jun. 2, 2020

(54) SYSTEM AND METHOD FOR RECIPE TO IMAGE ASSOCIATIONS

(71) Applicant: Under Armour, Inc., Baltimore, MD (US)

(72) Inventors: Chul Lee, San Francisco, CA (US); Jiaqi Sun, San Francisco, CA (US); Hesamoddin Salehian, San Francisco, CA (US)

(73) Assignee: Under Armour, Inc., Baltimore, MD (US)

( * ) Notice: Subject to any disclaimer, the term of this patent is extended or adjusted under 35 U.S.C. 154(b) by 216 days.

(21) Appl. No.: 15/826,169

(22) Filed: Nov. 29, 2017

(65) Prior Publication Data
US 2018/0157936 A1 Jun. 7, 2018

Related U.S. Application Data

(60) Provisional application No. 62/430,006, filed on Dec. 5, 2016.

(51) Int. Cl.
| | |
|---|---|
| *G06K 9/00* | (2006.01) |
| *G06K 9/62* | (2006.01) |
| *G16H 20/60* | (2018.01) |
| *G06N 3/08* | (2006.01) |
| *G06F 16/532* | (2019.01) |
| *G06N 3/04* | (2006.01) |

(52) U.S. Cl.
CPC ......... *G06K 9/6267* (2013.01); *G06F 16/532* (2019.01); *G06K 9/00671* (2013.01); *G06K 9/6201* (2013.01); *G06N 3/08* (2013.01); *G16H 20/60* (2018.01); *G06K 2209/17* (2013.01); *G06K 2209/506* (2013.01); *G06N 3/0454* (2013.01)

(58) Field of Classification Search
CPC .... G06K 9/6267; G06K 9/6201; G16H 20/60; G06F 16/532; G06N 3/08
See application file for complete search history.

(56) References Cited

U.S. PATENT DOCUMENTS

| | | | |
|---|---|---|---|
| 8,782,540 B2 * | 7/2014 | Turner | H04W 4/20 715/763 |
| 9,230,194 B2 * | 1/2016 | Rabinovich | G06K 9/66 |
| 9,514,331 B2 * | 12/2016 | Kanter | G06F 21/6245 |
| 9,928,448 B1 * | 3/2018 | Merler | H05K 999/99 |
| 2014/0337070 A1 * | 11/2014 | Cartwright | G06Q 50/01 705/7.12 |
| 2018/0157936 A1 * | 6/2018 | Lee | G06K 9/00671 |

\* cited by examiner

*Primary Examiner* — Gregory M Desire
(74) *Attorney, Agent, or Firm* — Law Office of Mark Wang, P.C.

(57) ABSTRACT

System and method for associating images to recipe records. In one embodiment, a method is provided which includes: receiving an uploaded photograph of a recipe image; and searching a database for an image which matches to the uploaded image. The database search may, in one embodiment, make use of a convolutional neural network (CNN)-based classifier. When one of the records in the database is identified as matching, providing a portion of the data associated to the record to the user device; receiving feedback from the user; and based on the feedback, providing a remaining portion of the data associated to the identified record to the user device for logging thereat; or enabling the user to create a new consumable item record.

18 Claims, 9 Drawing Sheets

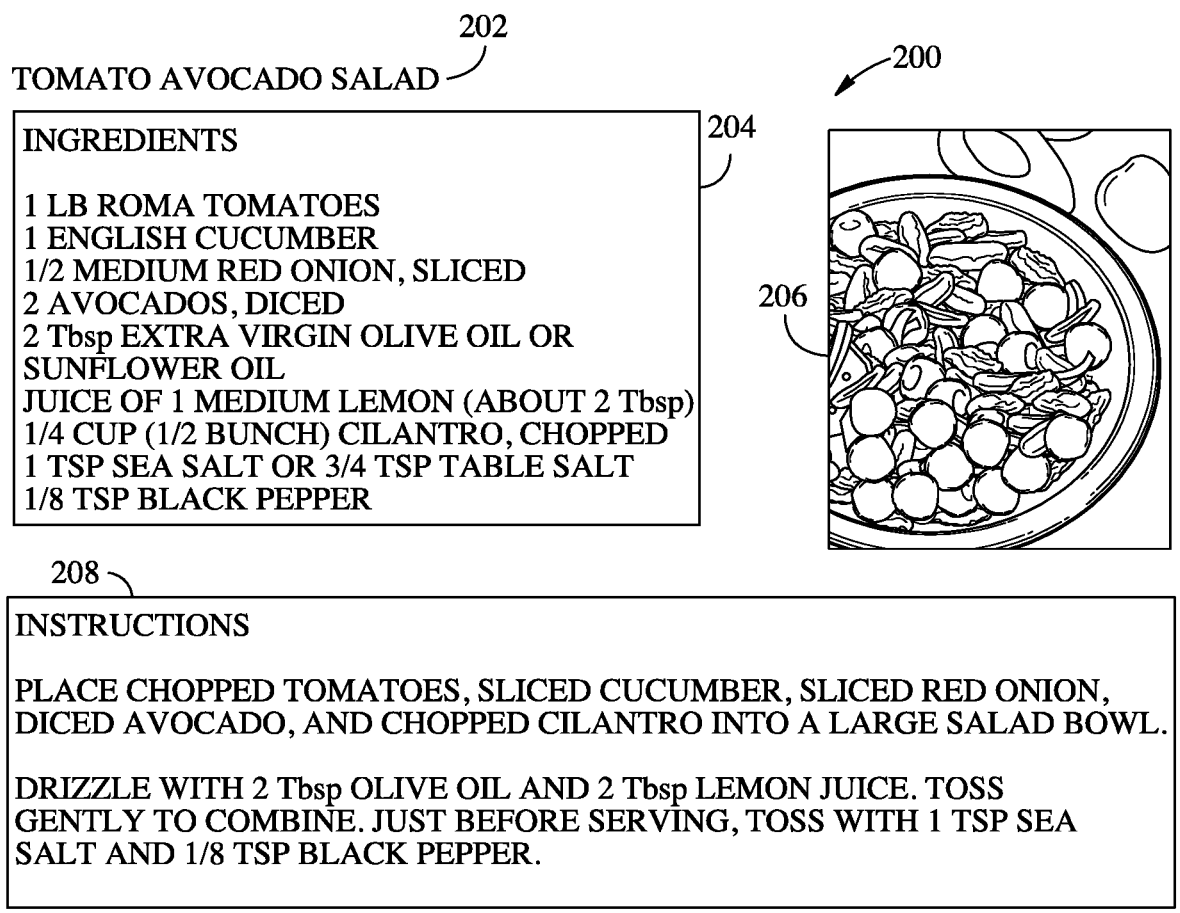

TOMATO AVOCADO SALAD

INGREDIENTS

1 LB ROMA TOMATOES
1 ENGLISH CUCUMBER
1/2 MEDIUM RED ONION, SLICED
2 AVOCADOS, DICED
2 Tbsp EXTRA VIRGIN OLIVE OIL OR SUNFLOWER OIL
JUICE OF 1 MEDIUM LEMON (ABOUT 2 Tbsp)
1/4 CUP (1/2 BUNCH) CILANTRO, CHOPPED
1 TSP SEA SALT OR 3/4 TSP TABLE SALT
1/8 TSP BLACK PEPPER

INSTRUCTIONS

PLACE CHOPPED TOMATOES, SLICED CUCUMBER, SLICED RED ONION, DICED AVOCADO, AND CHOPPED CILANTRO INTO A LARGE SALAD BOWL.

DRIZZLE WITH 2 Tbsp OLIVE OIL AND 2 Tbsp LEMON JUICE. TOSS GENTLY TO COMBINE. JUST BEFORE SERVING, TOSS WITH 1 TSP SEA SALT AND 1/8 TSP BLACK PEPPER.

FIG. 2A

SYSTEM AND METHOD FOR RECIPE TO IMAGE ASSOCIATIONS

PRIORITY

The present disclosure claims priority to co-owned, co-pending U.S. Provisional Patent Ser. No. 62/430,006; which is incorporated herein by reference in its entirety.

COPYRIGHT

A portion of the disclosure of this patent document contains material that is subject to copyright protection. The copyright owner has no objection to the facsimile reproduction by anyone of the patent document or the patent disclosure, as it appears in the Patent and Trademark Office patent files or records, but otherwise reserves all copyright rights whatsoever.

FIELD

This disclosure relates generally to the field of recipe capturing for nutrition logging. More particularly, the present disclosure relates to systems, computer programs, devices, and methods for enabling a user to conveniently log food via uploading an image associated with a recipe.

BACKGROUND

In recent years, health and fitness tracking applications that track food consumption have become very popular. Food consumption is important to a healthy lifestyle and is known to be related to various health conditions, such as diabetes and obesity to name a few. Health and fitness tracking applications allow users to set and achieve personalized health goals by tracking the foods and beverages that they consume. These applications enable users to gain insights that help them make smarter choices and create healthier habits.

However, food consumption tracking, even via computerized applications is often a time consuming and detailed process. Hence what is needed are improved methods for tracking or logging consumption data.

SUMMARY

The present disclosure addresses the foregoing needs by disclosing, inter alia, methods, devices, systems, and computer programs for providing a mechanism to associate recipe images to the ingredients and nutritional content of the food created by the recipe, thereby enabling a user to log or track consumption data more efficiently.

In one aspect of the disclosure, a method for enabling efficient association of a desired multi-ingredient consumable item to one of a plurality of multi-ingredient consumable item records in a database is given. In one variant, individual ones of the plurality of multi-ingredient consumable item records being associated to a plurality of data and at least one image, respectively. In one embodiment, the method comprises: (i) receiving at a server apparatus a photograph uploaded from a user device, the photograph comprising a photograph taken via a camera function of the user device of an image provided in association with a multi-ingredient consumable item; (ii) searching the database for an image which matches to the image of the uploaded photograph; (iii) when one of the individual ones of the plurality of multi-ingredient consumable item records is identified as being associated to the image which matches the uploaded photograph: (a) providing a portion of the data associated to the identified one of the individual ones of the plurality of multi-ingredient consumable item records to the user device; (b) receiving feedback from a user of the user device indicating whether the identified one of the individual ones of the plurality of multi-ingredient consumable items comprises the desired multi-ingredient consumable item; and (c) when the feedback indicates that the one of the identified one of the individual ones of the plurality of multi-ingredient consumable item records corresponds to the desired multi-ingredient consumable item, providing a remaining portion of the data associated to the identified one of the individual ones of the plurality of multi-ingredient consumable item records to the user device for logging thereat; and (iv) when none of the individual ones of the plurality of multi-ingredient consumable item records is identified as being associated to the image, or when the feedback indicates that the one of the identified one of the individual ones of the plurality of multi-ingredient consumable item records does not correspond to the desired multi-ingredient consumable item, enabling the user to create a new consumable item record.

In another aspect of the disclosure, a non-transitory, computer readable medium comprising a plurality of instructions are provided. In one embodiment, the plurality of instructions are configured to, when executed, cause a server device to: (i) receive a photograph uploaded from a user device, the photograph comprising a photograph taken via a camera function of the user device of an image provided in association with a multi-ingredient consumable item; (ii) search a database comprising a plurality of multi-ingredient consumable item records, individual ones of the records comprising a plurality of data and at least one image, the search comprising a search for an image which matches to the image of the uploaded photograph; (iii) identify one of the individual ones of the plurality of multi-ingredient consumable item records as being associated to the image which matches the image of the uploaded photograph; and (iv) provide a portion of the data associated to the identified one of the individual ones of the plurality of multi-ingredient consumable item records to the user device.

In yet another aspect, a network apparatus configured to enable efficient association of a desired multi-ingredient consumable item to one of a plurality of multi-ingredient consumable item records in a database. In one variant, individual ones of the plurality of multi-ingredient consumable item records being associated to a plurality of data and at least one image, respectively. In one embodiment, the apparatus comprises: one or more transceivers; a storage apparatus; and a processor configured to execute at least one computer application thereon. In one embodiment, the computer application comprises a plurality of instructions which are configured to, when executed, cause the network apparatus to: (i) receive a photograph uploaded from a user device, the photograph comprising a photograph taken via a camera function of the user device of an image provided in association with a multi-ingredient consumable item; (ii) search the database for an image which matches to the image of the uploaded photograph; (iii) when one of the individual ones of the plurality of multi-ingredient consumable item records is identified as being associated to the image which matches the image of the uploaded photograph: (a) provide a portion of the data associated to the identified one of the individual ones of the plurality of multi-ingredient consumable item records to the user device; and (b) receive feedback from a user of the user device indicating whether the identified one of the individual ones of the plurality of multi-ingredient consumable items comprises the desired multi-ingredient consumable item.

These and other aspects of the disclosure shall become apparent when considered in light of the disclosure provided herein.

BRIEF DESCRIPTION OF THE DRAWINGS

FIG. 2A is block diagram of an exemplary recipe in accordance with one embodiment of the present disclosure.

Figure 1:
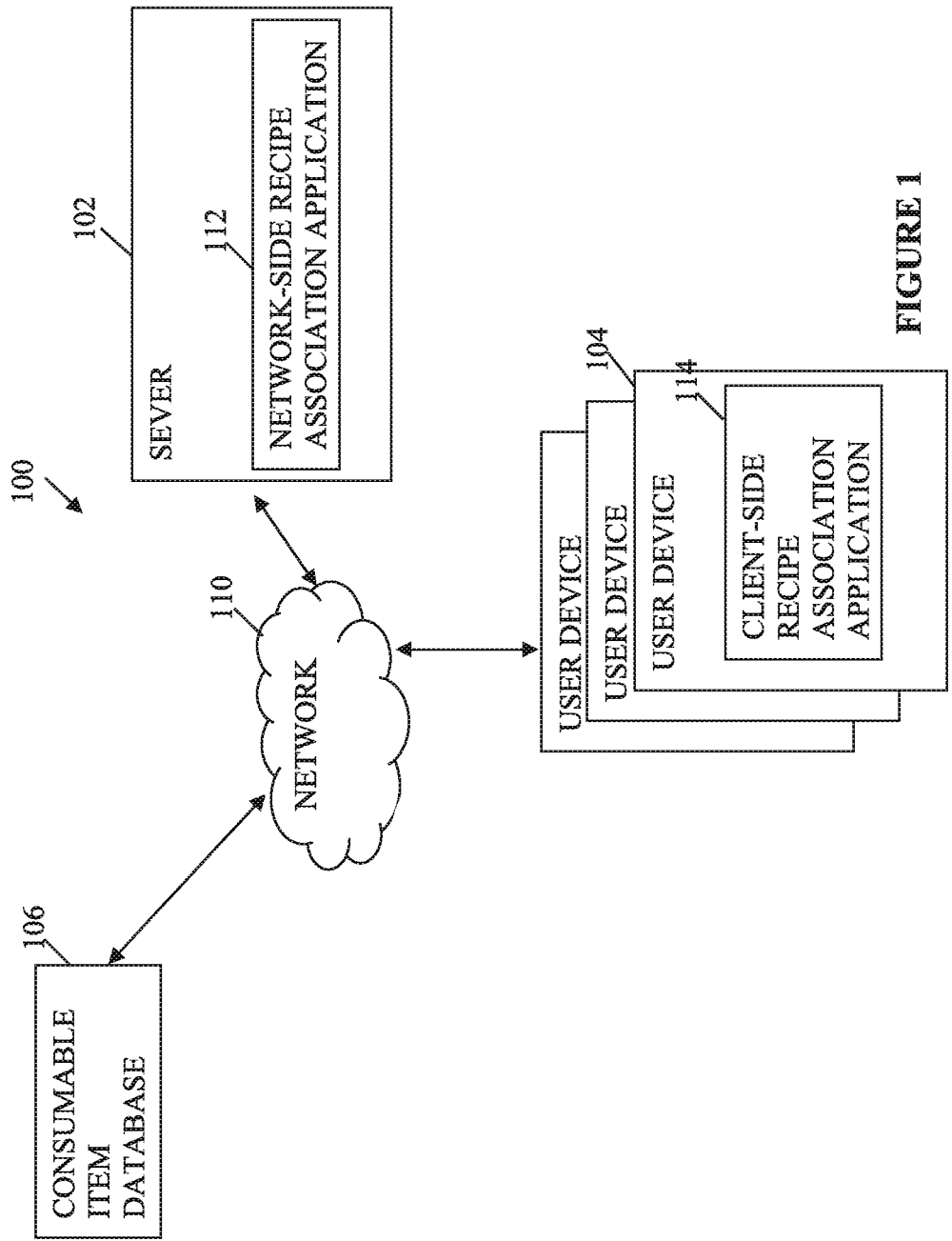
FIG. 1 is a block diagram illustrating an exemplary system for enabling association of recipe images in accordance with one embodiment of the present disclosure.

All Figures © Under Armour, Inc. 2016. All rights reserved.

DETAILED DESCRIPTION

Disclosed embodiments include systems, apparatus, methods and storage media which associate recipe images to the ingredients and nutritional content of the food created by the receipt, thereby enabling a user to log or track consumption data more efficiently.

In the following detailed description, reference is made to the accompanying drawings which form a part hereof wherein like numerals designate like parts throughout, and in which is shown, by way of illustration, embodiments that may be practiced. It is to be understood that other embodiments may be utilized, and structural or logical changes may be made without departing from the scope of the present disclosure. Therefore, the following detailed description is not to be taken in a limiting sense, and the scope of embodiments is defined by the appended claims and their equivalents.

Aspects of the disclosure are disclosed in the accompanying description. Alternate embodiments of the present disclosure and their equivalents may be devised without parting from the spirit or scope of the present disclosure. It should be noted that any discussion herein regarding "one embodiment", "an embodiment", "an exemplary embodiment", and the like indicate that the embodiment described may include a particular feature, structure, or characteristic, and that such particular feature, structure, or characteristic may not necessarily be included in every embodiment. In addition, references to the foregoing do not necessarily comprise a reference to the same embodiment. Finally, irrespective of whether it is explicitly described, one of ordinary skill in the art would readily appreciate that each of the particular features, structures, or characteristics of the given embodiments may be utilized in connection or combination with those of any other embodiment discussed herein.

Various operations may be described as multiple discrete actions or operations in turn, in a manner that is most helpful in understanding the claimed subject matter. However, the order of description should not be construed as to imply that these operations are necessarily order dependent. In particular, these operations may not be performed in the order of presentation. Operations described may be performed in a different order than the described embodiment. Various additional operations may be performed and/or described operations may be omitted in additional embodiments.

For the purposes of the present disclosure, the phrase "A and/or B" means (A), (B), or (A and B). For the purposes of the present disclosure, the phrase "A, B, and/or C" means (A), (B), (C), (A and B), (A and C), (B and C), or (A, B and C). Similar logic applies to the use of the term "or" herein; i.e., "A or B" means (A), (B), or (A and B).

The terms "comprising," "including," "having," and the like, as used with respect to embodiments of the present disclosure, are synonymous.

Network Architecture

There exists a persistent need to provide efficient and easy-to-use mechanisms for enabling a user to enter consumed items into a nutrition log or tracking application. This is especially necessary when the consumed item has multiple ingredients, such as a recipe, as logging multi-ingredient items generally relies on entry of each ingredient individually. In order to provide for efficient entry thereof, the present disclosure provides a system for associating recipes to images as discussed herein.

Referring now to FIG. 1, an exemplary system associating multi-ingredient consumable items (i.e., recipes) to images is shown. As illustrated, the system generally comprises a server apparatus 102 in communication with one or more user devices 104 and a consumable item database 106 via a network 110.

The network 110 which enables communication between the server 102, the plurality of user devices 104, and the consumable item database 106 (each discussed in turn below) may comprise one or more wired and/or wireless, private and/or public network, including but not limited to, e.g., the Internet. The network 110 is, for example, a wireless local area network (WLAN), wireless wide area network (WWAN), wired network, or any other suitable communication channel. Accordingly, each of the user devices 104, server(s) 102, and consumable item database 106 are configured with appropriate networking communication interfaces. An example of wired communication interface may include, but is not limited to, Ethernet; while examples of wireless communication interfaces may include, but are not limited to, near field communication (NFC), Bluetooth, WiFi, 4G or 5G LTE. It is further appreciated that various gateways, routers, switches, base stations, and so forth may be involved in facilitating and forwarding communication between the foregoing devices. Additionally, it is noted that the foregoing network may comprise several networks, such that the described components are distributed in various ones thereof. In alternative embodiments, the network may comprise a series of devices communicating within software via software API's.

The user devices 104, in one exemplary implementation, comprise one or more portable computerized devices which are configured to measure, obtain, monitor, generate, collect, sense, or otherwise receive biometric, environmental, activity and/or health parameters. In an exemplary embodiment, the specific health parameter which is obtained comprises a user's eating habits. Hence, the user devices 104 are specifically configured to enable a user to enter one or more consumed items for logging/tracking. User devices 104 may also be referred to herein as health and/or activity monitoring devices. In one variant, certain ones of the user devices 104 comprise wearable health-related parameter measurement and computing devices, such as e.g., a smart watch, an activity tracker, a heart rate monitor, a sleep tracking device, a nutrition tracking device, a smart scale, and/or smart eyeglasses. In addition, an exemplary user device 104 may comprise a smartphone having one or more of the foregoing capabilities and/or which enables user entry of the foregoing health data. Alternatively, the user device 104 is in communication with a health and/or activity monitoring device.

The sensed health parameter data comprises data which the particular device 104 is configured to collect (such as activity, biometric, and environmental data). For example, an activity tracking device is configured to collect activity data such as steps taken, distance travelled, rate or pace of a run, and/or flights of stairs climbed, etc.; a heart rate monitor is configured to collect heartbeat data; a sleep tracking device collects data relating to how much time a user/wearer spends sleeping; a nutrition tracking device collects data relating to food and drinks consumed by a user; a smart scale collects data relating to a body weight, body fat percentage, and/or body mass index (BMI), etc. Furthermore, a smartwatch and/or smartphone, may be utilized as an activity tracking device, a heart rate monitor, a sleep tracking device, and/or a nutrition tracking device. The user device 104 may comprise any of the foregoing types of devices and/or may receive collected data from a first device at one or more applications running on the user device 104.

The exemplary user device 104 may be further configured enable entry and/or display of collected data. In such instances, the exemplary user device 104 may run one or more applications configured to process (e.g., transform) the collected data. Exemplary applications include e.g., UA Record®, MapMyFitness®, MyFitnessPal®, Endomondo®, etc. each owned by assignee hereof. Other health activity related monitoring applications may additionally be utilized in connection with the present disclosure, such as those specifically designed to receive information from a particular type of health monitoring device (i.e., an application which is published by the device manufacturer); the foregoing being merely representative of the general concepts of the present disclosure.

As will be discussed in greater detail below, in one exemplary embodiment the application(s) running at the user device 104 which are configured to receive e.g., nutrition tracking data and/or consumption data utilize at least one client-side recipe association application 114. The client-side recipe association application 114 is configured to enable a user to track or log consumed items. As discussed in greater detail below, the client-side recipe association application 114 enables a user to quickly and accurately account for the nutritional content of a multi-ingredient recipe using image recognition in one exemplary embodiment. The term "recipe" is used herein to refer to a multi-ingredient consumable item.

The server 102 as illustrated in FIG. 1 comprises one or more computerized devices operable to enable a user at a client device 104 to via a photograph of a recipe image, obtain highly accurate nutritional information relating to a recipe. To this end, as shown, the exemplary server 102 comprises at least a network-side recipe association application 112. The network-side recipe association application 112 is utilized in conjunction with a corresponding application at the user device 104 (i.e., recipe association application 114) to enable the herein disclosed features. Specifically, it is via the coordination of the network-side application 112 and client-side application 114 that a user is able to upload a recipe image, have the image evaluated against other images to determine a recipe to which it likely matches, and pull from the most likely match accurate nutritional information for logging at the user device 104. Additional features and components of the server 102 will be discussed in further detail below.

The consumable item database 106 comprises a database or store of data records. The data records comprise detailed nutritional information relating to consumable items, which may include single ingredient items (such as fruit, vegetables, etc.) as well as multi-ingredient items (such as recipes, menu items, meals, etc.). These records are uploaded to the database 106 from various sources including e.g., individual users (via user devices 104), manufacturers or providers of the consumables represented by the data records, government or other third party databases, etc. To this end, multiple entries may exist for a single consumable item. As will be discussed herein, the present disclosure enables accurate and efficient identification of a best match from among the data records to a particular multi-ingredient item.

In addition to the nutritional information contained in the data records relating to consumable items, in certain instances the data records may further include one or more images. These images are particularly relevant to the present discussion, especially, with respect to multi-ingredient consumable items. Specifically, in one embodiment of the present disclosure, a user is able to upload an image of a recipe, and that image is searched against the images associated to records in the database 106. As will be discussed in greater detail below, a matching image may be identified using deep learning/convolutional neural networks (CNN). Then, based on the match, the nutritional information and other details from the matching record are provided to the user to be used in logging/tracking (as discussed below).

It is appreciated that in the illustrated embodiment, the consumable item database 106 comprises a separate entity in communication with server 102 and user device(s) 104. However, in other variants, the consumable item database 106 may be provided in part or in whole to the user device 104 for storage thereat. For example, data records which have been utilized at a particular user device 104 may be stored thereat. Additionally, or in the alternative, the consumable item database 106 (in whole or in part) may be stored at the server 102 and portions thereof may be made accessible to particular devices 104. Any combination of the foregoing configurations may be utilized with equal success.

Exemplary user interfaces for enabling the previously referenced accurate and efficient identification of a best match from among the data records to a particular multi-ingredient item are discussed in further detail below.

Exemplary Interfaces

The features of the present disclosure are described in one exemplary embodiment according to FIGS. 2A-2D. As noted above, the term "recipe" is used to correspond to a multi-ingredient consumable item. As shown, at FIG. 2A an exemplary recipe card 200 is provided having a title 202, an ingredient list 204, an image 206, and cooking instructions 208. It is appreciated that, although the present card 200 provides a recipe for "Tomato Avocado Salad" other recipe cards (not shown) may be used to accomplish the features discussed in the present disclosure with equal success. In one variant, the recipe cards may have a similar structure or format to that of FIG. 2A, and at a minimum include an ingredient list 204 and a recipe image 206. Additionally, such recipe cards may be provided in the form of a book (e.g., cookbook), a website or webpage, product packaging, mobile applications, etc. The recipe image 206 discussed throughout the present disclosure, in one embodiment, comprises an image generated by the recipe creator and published with the same recipe uniformly to represent the completed recipe. It is appreciated, however, that in one or more alternative embodiments, users may provide images of the recipes they have completed themselves, i.e., which are not standard and/or uniform but rather indicative of the user's attempt to recreate the recipe.

Figure 2B:
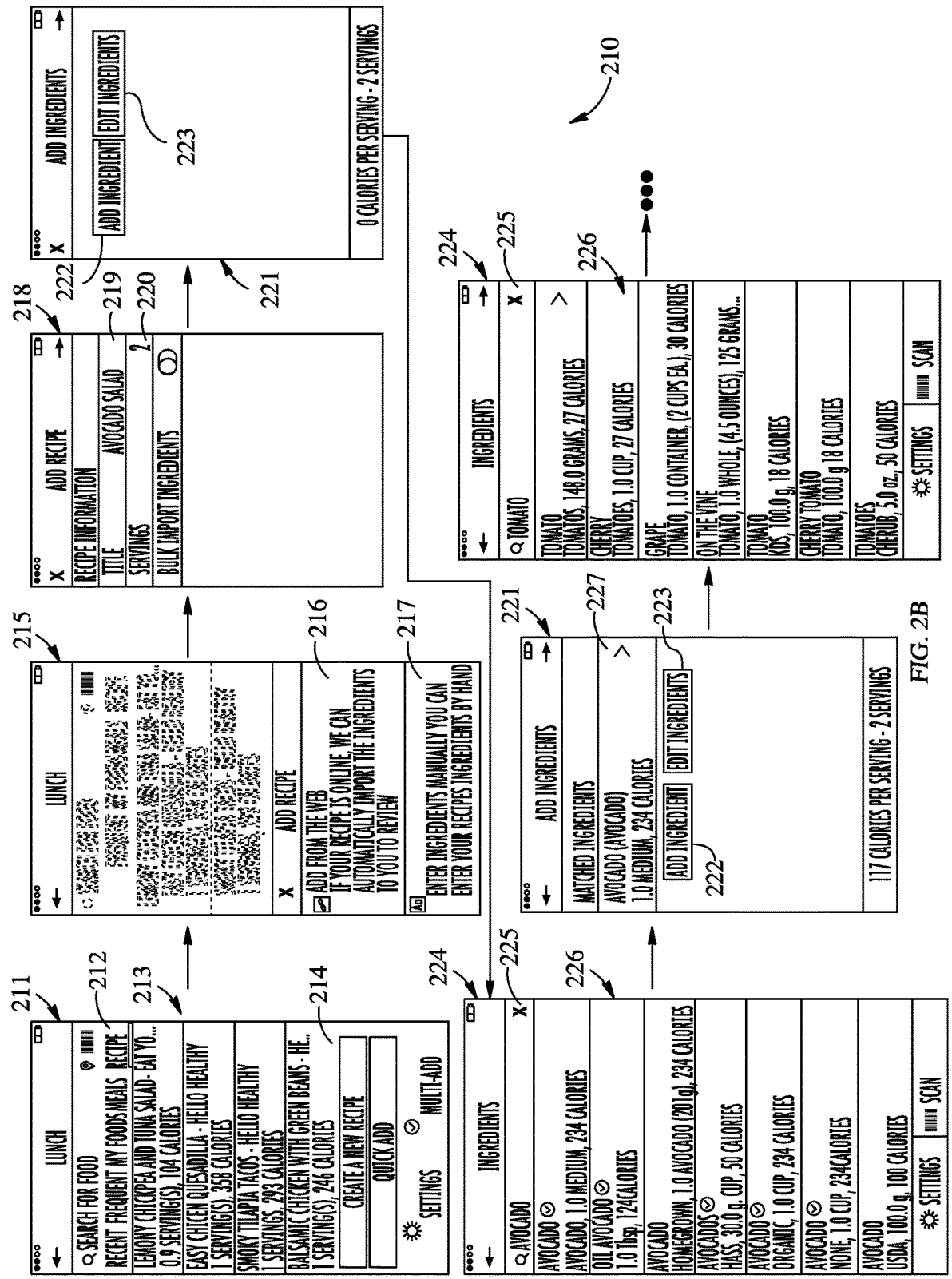
FIG. 2B is an application diagram illustrating an exemplary user flow for entering the components of a recipe to be logged in accordance with one embodiment of the present disclosure.

FIG. 2B provides an exemplary interface flow 210 when a user seeks to log the recipe represented by the card 200 as a consumed item in a health or nutrition tracking application without the use of image recognition. As shown, at a food entry landing interface 211, the user is presented with this page 211 when he/she navigates to a particular meal (in this case lunch) to enter or log consumed items. Across the top row of options, the user is provided with several options 212 including e.g., an option to review frequently logged items, saved items, saved meals and saved recipes. Additional options 212 may be provided including e.g., recently logged items. As shown the food entry landing interface 211 provides a list of entries 213 which match the particular option 212 to which the user has navigated to be displayed. For example, when the user navigates to the "frequent" option 212, summarized data relating to one or more consumable data records that are frequently selected by the user are displayed. Similar logic applies to the saved meals, saved items (e.g., "My Foods"), etc. In the illustrated embodiment, the list of saved entries 213 include saved recipes because the user has navigated to the recipe option 212.

At the food entry landing interface 211, the user may select an option to create a new recipe 214. Upon such selection, the user is presented with a recipe addition interface 215. As shown, at this interface the user may elect to add a recipe from a website 216 and/or to add the ingredients manually 217. Assuming that the user selects to add the ingredients manually (via option 217), he/she is then presented with a recipe detail landing page 218. The recipe detail landing page 218 includes a field for the user to enter a title for the recipe 219, a field for the user to enter a number of service 220. Once these are entered, the user may navigate to a page for adding ingredients 221. At this page 221, the user may press a button to add ingredients 222 and/or a button to edit existing ingredients 223.

When the user selects to add an ingredient (via button 222), he/she is provided to an ingredient search interface 224. At this interface 224, the user may use text or spoken language to enter a search term in the search bar 225. In the illustrated example, the user has searched for the ingredient: avocado. Accordingly, a list of results 226 are provided. The user reviews the list of ingredients to determine an entry which most closely matches the desired recipe ingredient and selects the entry. Upon such selection, the ingredient is added and therefore is displayed 227 at the ingredient addition page 221.

At the ingredient addition page 221 the user will continue to select to add ingredients 222 until all of the recipe ingredients are added (e.g., next the user may search for and add tomatoes, etc.). Therefore, the interface flow 210 continues or repeats as necessary. Once the ingredients have all been added, the user may save the recipe for future selection. Since the interface flow of FIG. 2B must be repeated for every ingredient in a multi-ingredient recipe, the present embodiment may be most useful for multi-ingredient consumable items having only a few ingredients. In other words, it may become cumbersome or burdensome for a user to log or track food this way when the consumable item to be logged or tracked has a larger list of ingredients. Accordingly, the exemplary interface flow of FIG. 2C is provided which utilizes image recognition to speed the process of ingredient entry, as discussed below.

Figure 2C:
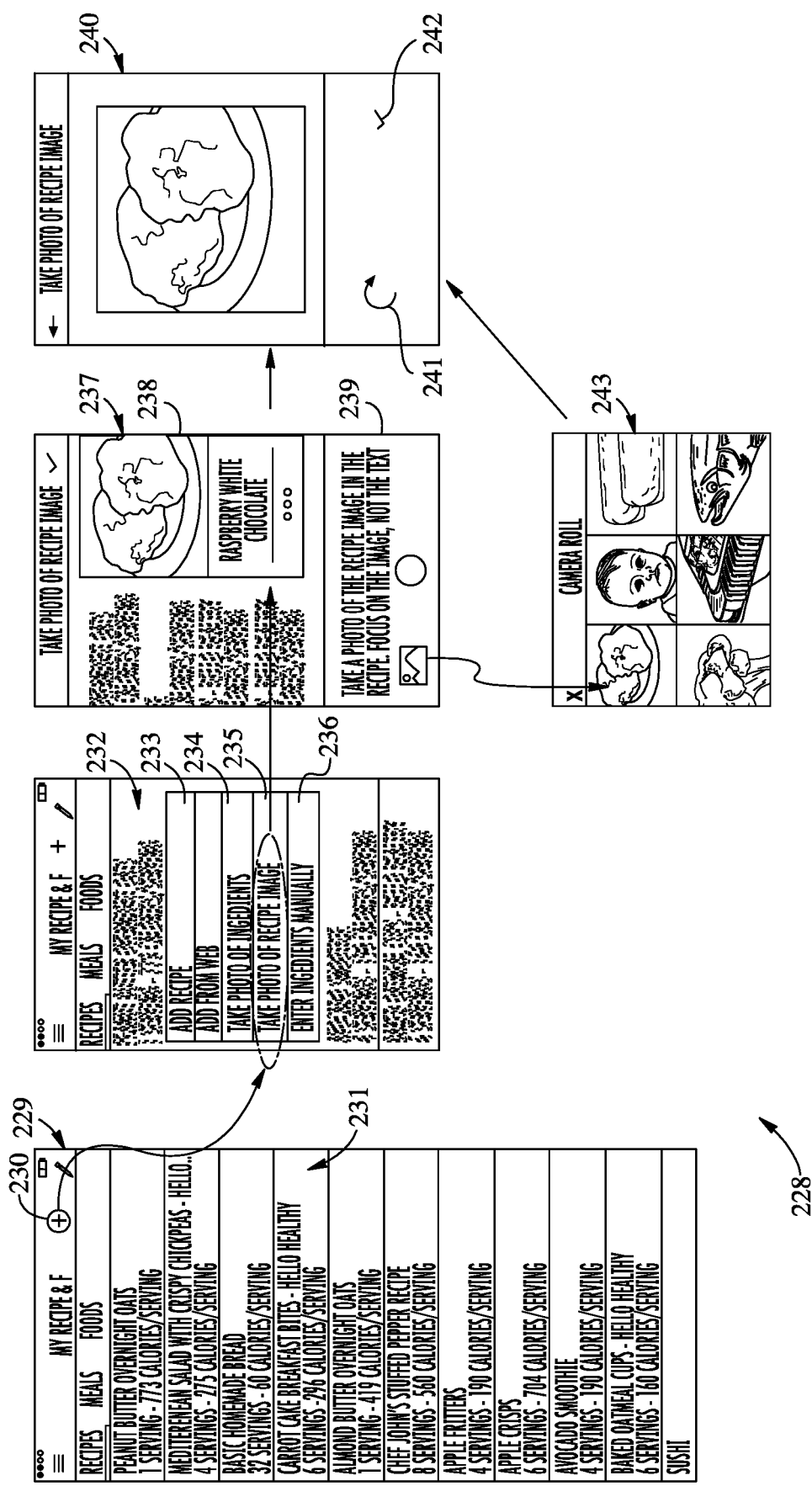
FIG. 2C is an application diagram illustrating another exemplary user flow for entering the components of a recipe to be logged in accordance with one embodiment of the present disclosure.

According to the interface flow 228 of FIG. 2C, a user first navigates to a page for reviewing saved recipes, meals, food, etc. 229. At the saved item page 229, the user is given an opportunity to select from a list of previous recipes 231. Additionally, the user is given an opportunity to add a new recipe via a selectable icon 230. When the user selects the icon 230 to add a new recipe, an interface for adding options 232 is provided.

The options to add a recipe at the recipe adding interface 232 include an option to add the recipe from a webpage 233, take a photograph of an ingredient list 234, take a photograph of a recipe image 235, or enter the ingredients manually 236. It is noted that in the instance the user elects to enter the ingredients manually via a selection at 236, an interface flow similar to that discussed above with respect to FIG. 2B is followed.

In the instance the user selects to add the recipe from a web page via a selection at 233, the webpage is identified and the ingredients are populated from the identified website. Specifically, the text description of the ingredients are used in multiple automatic queries from the server-side recipe association application 112 to a consumable item database 106. In one embodiment, queries for each of the individual ingredients are made simultaneously. Next, one or more identified records in the database 106 are identified. In one variant, the one or more identified records may be presented to the user at the user device 104 for verification (such as via the client-side recipe association application 114). Alternatively, a most frequently selected record may be automatically applied, and the user may be given an option (via the client-side recipe association application 114) to review other similar entries if desired. That is, the user may click on, or select an automatically applied recipe ingredient to review the item details (including nutritional content, calories, and serving size), the user may then edit the existing record or select an option to run a query for the ingredient again and therefore receive a list of closely matching items from the database 106. The user may then select and/or edit the automatically selected item, or one of the newly presented items. In addition, the network-side recipe association application 112 may automatically adjust or apply a serving size to the selected record as determined from the online or website provided recipe. For example, if a particular online recipe calls for two large apples, the network or server-side application 112 will provide a query to the database 106 for "large apple", "apple" or "apples". Based on the results that are received, the network-server or the user him/herself may select a particular data record for a single large apple, in this instance the serving size is doubled to account for the recipe's requirement for two large apples.

In the instance the user selects to add the recipe from a photograph of the ingredients via a selection at 234, many of the same logic which applied to the instance that the recipe was obtained from a website is utilized. However, in this instance, the client-side application 114 may utilize optical character recognition (OCR) to determine text from the image of the recipe ingredients. The text is then used in a series of queries to the database 106 similar to the queries discussed above. A list of results and/or a selection of one of the results is provided to the user, then as noted above, the user may edit the selected item and/or select a different item to correspond to the recipe ingredient. Similar to the discussion above, the network-side application 112 may further adjust the serving size based on the amounts listed in the recipe.

Finally, in the instance the user selects to add the recipe from a photograph of the recipe via a selection at 235, an image uploader is provided 237. It is appreciated that the image uploader 237 may also be provided in the instance the user elects to add the recipe from a photograph of the ingredients (discussed above). As shown, the image uploader 237 accesses a camera within the user device 104 to enable the user to take a picture of an image 238 from the recipe card. The image uploader 237 further provides instructions to the user relating to the desired qualities of the image (e.g., no text, centered on the photo, etc.). As shown at item 243, at the image uploader 237, the user may elect to access the device 104 camera roll 243 in order to obtain a previously captured recipe image. In either instance (i.e., the instance the user selects an image from the camera roll 243 or the instance the user takes a photograph at the image uploader page 237), the user is next provided with a confirmation screen 240. At the confirmation screen 240, the user may accept 242 or reject 241 the photograph.

Figure 2D:
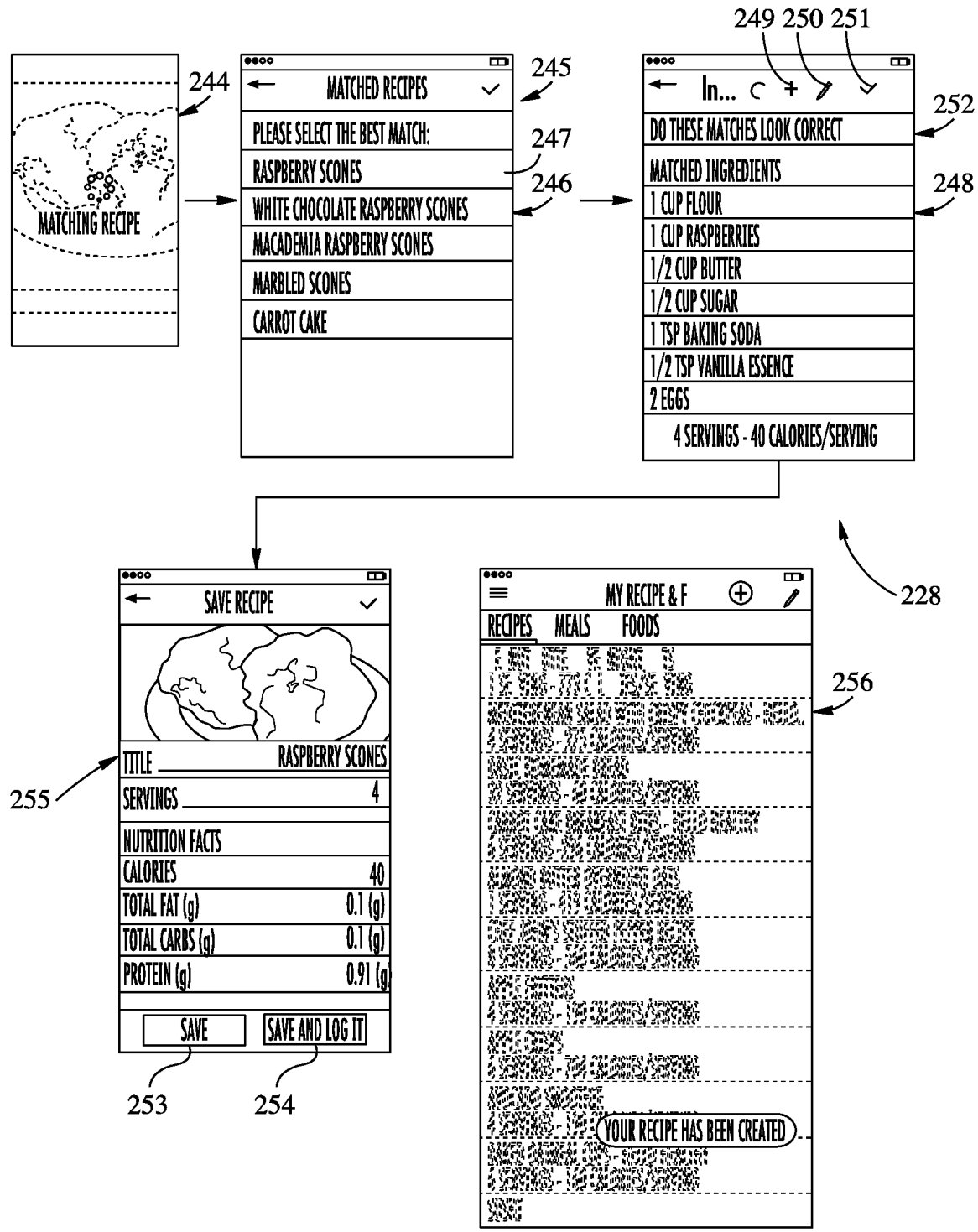
FIG. 2D is an application diagram illustrating another exemplary user flow for entering the components of a recipe to be logged in accordance with one embodiment of the present disclosure.

When the user accepts a photograph 242, the process flow 228 continues as shown in FIG. 2D. As shown, the user's selection of the photograph causes a query to be made to the consumable item database 106. Specifically, the query comprises the photographed image which matched to images in the database records. As the query is performed, the user is shown a waiting screen 244.

Once a match is determined, a list of matched recipes 246 is displayed to the user at the display 245. In one variant, the list 246 includes the top few items (e.g., five as shown in FIG. 2D) which most closely correlate to the uploaded image. As will be discussed in greater detail below, the determination of a match comprises utilization of pattern recognition, machine learning, convolutional neural networks (CNN) and/or deep learning techniques. Accordingly, mechanisms are provided to match the uploaded image to an image in the database 106, then information from the data record associated to the closest matching image is provided at the display 245 (in the illustrated embodiment, only the consumable item title is provided at this display 245; however it is appreciated that other information including e.g., summarized nutrition information or an ingredient list may also be provided). The user selects at least one of the items from the list 246 which best represents the recipe which is to be logged or tracked in the health monitoring application (such as may be incorporated into the recipe association application 114).

Upon selection at display 245, an ingredient list 248 for the selected recipe is displayed at an ingredient confirmation interface 242. At the ingredient confirmation interface 247, the user is able to review the ingredients of the selected recipe. The user may edit one or more of the ingredient entries by selecting the edit icon 250, may add additional ingredients by selecting the add icon 249, and may confirm the ingredient list by selecting the confirmation icon 251.

When the user selects to add additional ingredients 249, similar flows to those discussed above may be utilized. That is, in one embodiment the user may add additional ingredients via a manual search. Alternative means for adding additional ingredients may be utilized with equal success, including e.g., addition thereof via a picture or web site. When the user selects to edit the ingredients 250, the user is taken to an interface for the ingredient having designations of which values for the ingredient, if any, may be edited. Commonly, the user will be able to edit the serving size of an ingredient.

When the user confirms the ingredient list 251, i.e., has determined that each of the ingredients belongs in the recipe and that each ingredient has an appropriate serving size, etc., the user is taken to a confirmation page 255. At the confirmation page 255, the user may view the image and other details of the recipe (such as title, number of servings, nutritional totals, etc.). The user may also press a button 253 to save the recipe and, in the illustrated embodiment, press a second button 254 to save the recipe and log the item in his/her nutrition or diet diary. Thereafter, the new recipe will be saved to the saved recipes page 256.

Exemplary methods for enabling the previously referenced accurate and efficient identification of a best match from among the data records to a particular multi-ingredient item are discussed in further detail below.

Methodology

Figure 3:
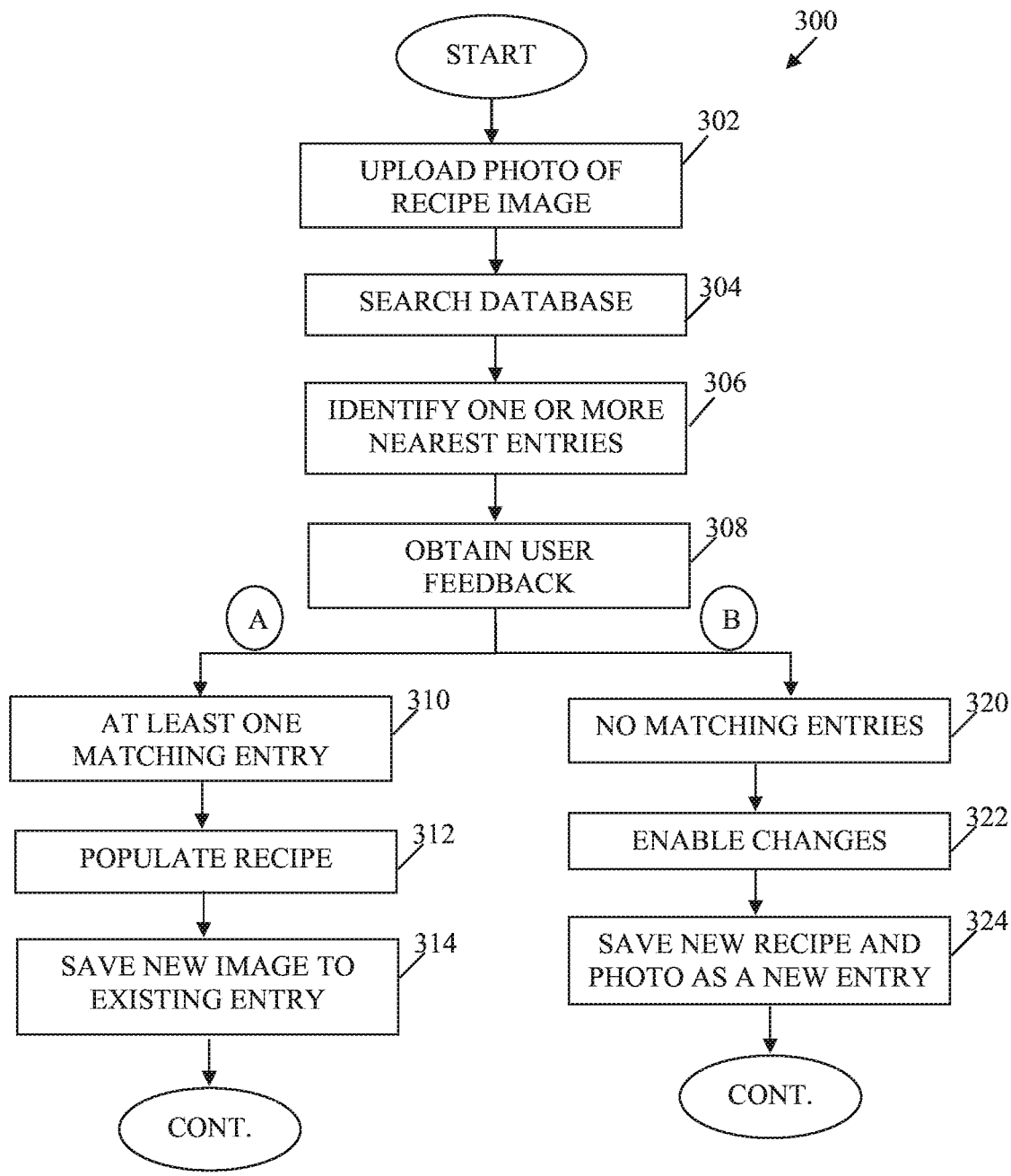
FIG. 3 is a logical flow diagram illustrating an exemplary method for enabling recipe image associations in accordance with one embodiment of the present disclosure.

Referring now to FIG. 3, an exemplary method 300 for enabling recipe image associations in accordance with one embodiment of the present disclosure is given. As shown, per step 302, a user uploads a photograph of a recipe image. In one embodiment, this may be accomplished via the user interfaces discussed above with respect to FIGS. 2C-2D. The uploaded image is compared against a database of images to find one or more matching images (step 304). Exemplary mechanisms for such comparison are discussed in greater detail below. When one or more nearest entries are identified at step 306, they are presented to the user to obtain feedback 308. Such feedback may be in the form of a selection of one or more presented items. The system discussed herein may be configured, in one embodiment, to use the feedback to train or otherwise make the selection process more accurate (as discussed elsewhere herein).

In one specific embodiment, the identified entries at step 306 are provided for display at the user device 104 via the client-side recipe association application 114. The identified entries may include an image associated to the entry as well as details relating to the entry including e.g., a title or name, ingredients, nutrition facts, serving size, a source of the entry, etc. Based on the information presented via the display, the user may indicate that at least one entry matches the desired recipe (pathway A, step 310), or that none of the entries matches the desired recipe (pathway B, step 320). In the embodiment illustrated at FIG. 2D, a list of titles of potentially matching recipes 245 is provided. In other alternative embodiments, one or more details may be provided instead of or in addition to the title of the recipe including e.g., the images, the ingredients, the serving size, etc.

When it is set forth by the user that at least one of the identified entries matches the desired recipe (pathway A, step 310), the recipe details are populated based on those of the match (step 312). Following the example set forth in FIG. 2D, when the user selects the first item on the list 247, for "Raspberry Scones", based on this selection (step 310), the recipe details are populated (step 312). In other words, the ingredients for the recipe are provided at screen 252. The user may edit or otherwise add/remove ingredients and once completed is taken to a summary screen 255 where the user may edit a number of servings of the recipe he/she consumed to have the nutritional data saved to the user's log. The user may also save the recipe for future use.

Next, at step 314, the new image (i.e., the image uploaded by the user) may be saved to the existing recipe entry. As discussed herein, having several images linked to a single recipe enables a user to select a recipe based on the best matching photograph. Additionally, such a system enables the system to accurately identify a photograph match based on a review of an uploaded image against a plurality of existing photographs for each recipe item. However, in another embodiment, this step may be skipped or omitted as being redundant to the image(s) that are associated to each recipe prior to the upload.

In the event that the user is not able to identify a matching recipe from the identified nearest entries (step 320), i.e., the user indicates that there are no matching entries, the user may be provided with the details relating to the next nearest recipe as determined at step 306. The user may then be provided with a means to make changes to the recipe provided in order to arrive at a recipe for the actual consumable item he/she desires (step 322). Once the user has edited the recipe to arrive at a new recipe, it is saved at step 324 along with the photograph that the user uploaded to create a new record. The user may be provided with a similar interface to that discussed above at screen 252 of FIG. 2D for enabling editing of the ingredients of a next nearest recipe which doesn't quite match the desired recipe.

As discussed above, FIG. 3 provides a method 300 for enabling an image based search for recipes. In another embodiment, shown at FIG. 4, a method 400 may be provided for enabling a search based on recipe details (e.g., title, ingredients, etc.) to be matched to an existing recipe and its associated image (optional).

As shown, at step 402 of the method 400 the user begins by entering one or more recipe details, such as a recipe name, ingredients, source, etc. as the details are entered, a back-ground search of the consumable item database 106 is performed (step 404). For example, if the user enters the first ingredient of "chicken breast", several entries may be identified including e.g., chicken parmesan, chicken salad, fried chicken, chicken enchiladas, etc. Next, at step 406 it is determined whether any of the entries identified via the search are significantly near to the entered recipe details. This may be performed using a computer analysis or via human (i.e., user) decision-making. In another variant, the aforementioned OCR techniques may be utilized such that the user may upload a picture or image of the text of the recipe, the ingredients are obtained therefrom and utilized as discussed herein.

In the instance the determination at step 406 is performed via computer analysis, rules may be put in place to narrow down a list of possible entries. For example, these rules require a minimum number of recipe details to be entered before a list or individual recipe may be identified as being significantly near to the desired consumable item; in another embodiment the rules may require that the returned results from a search of the database be within a predetermined range (e.g., 5 entries or fewer) before a list or individual recipe may be identified as being significantly near to the desired consumable item. In yet another embodiment, the rules may indicate that a certain percentage of recipe details must be within a given percentage error in order for a recipe to be selected as a nearest match. For example, a recipe for chicken salad may include only two chicken breasts, whereas a recipe for fried chicken may include 4-6 chicken breasts. Hence, a user's entry of 1.5 chicken breasts would indicate to the analysis system that the user is more likely making chicken salad and not making fried chicken. Other rules may be utilized with equal success.

In the instance the determination at step 406 is performed by a human, in one embodiment, a list of possibilities is displayed to a user. The list may be updated as the user enters additional recipe details. For example, when the user enters the first ingredient of "chicken breast" a larger list of possible entries may be provided including e.g., chicken parmesan, chicken salad, fried chicken, chicken enchiladas, etc. It is appreciated that in one embodiment, such a list may only be provided when it is first determined by the computer analysis system that the number of entries in the list is within a predetermined range (e.g., 100 or fewer), as noted above.

When there is at least one entry identified as being significantly near to the desired consumable item (whether determined via computer analysis, user input, or a combination of these), the method 400 then proceeds to step 408 wherein the remaining recipe details are populated. In addition, at step 410, the image of the existing identified recipe may be optionally associated to the user's entry. As noted above, and demonstrated in FIG. 2D, the user may further edit the populated recipe information including editing an amount of each ingredient, removing or adding ingredients, adjusting a serving size, etc. These edits are used to finalize the nutrition information presented to the user and saved in the user's food log.

When there cannot be identified at least one entry as being significantly near to the desired consumable item, the method 400 continues to step 412 where it is determined whether there are any additional recipe details to be entered. When additional details remain, the method 400 continues so that these details are entered (step 402) and searched (step 404) as discussed above. A new determination at step 406 is based on the updated recipe details according to this embodiment. Continuing the example above, if the second ingredient entered by the user comprises "flour", the list may be narrowed to include chicken parmesan, fried chicken, and chicken enchiladas. However the amount of flour in a typical chicken enchilada recipe is far less than that needed for chicken parmesan and/or fried chicken. Therefore, the computer analysis system may at step 406 remove chicken enchiladas from the list for being outside of the tolerance level for an amount of that ingredient.

When there remain no more additional details for the user-entered recipe, the method 400 proceeds to create a new recipe for the user-entered ingredients at step 414. A photograph associated to the recipe may optionally be uploaded and associated to the new entry at this step as well.

Using the system discussed herein, a given user-entered recipe is more likely to find a match when a threshold number of ingredients or other recipe details are provided. Hence, in another embodiment, the method 400 may be modified to only populate a recipe (step 408) when a threshold amount of information regarding the recipe has been provided. In other words, the determination as to whether an entry having significant nearness to an existing entry is only answered in the affirmative when the user has entered sufficient detail regarding his/her desired recipe.

Figure 4:
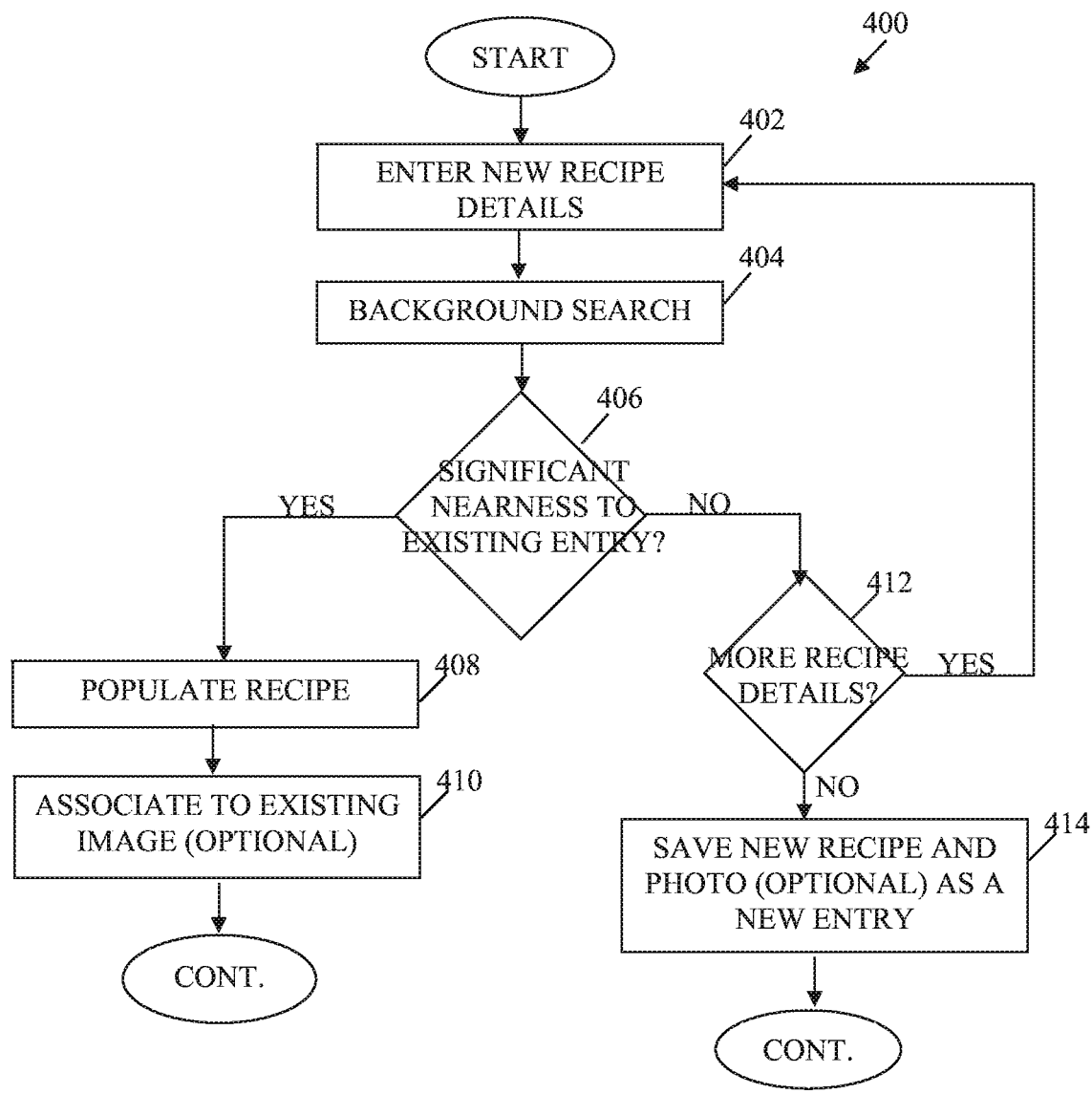
FIG. 4 is a logical flow diagram illustrating another exemplary method for enabling recipe image associations in accordance with one embodiment of the present disclosure.

It is noted that significant portions of the methods 300 and 400 of FIGS. 3 and 4, respectively may be performed at the network-side recipe association application 112 of the server apparatus 102, using entries, inputs, and images uploaded via the client-side application 114 at a client or user device 104. Exemplary apparatus including an exemplary client device 104 and an exemplary server 102 are now discussed with reference to FIGS. 5-6 below.

Exemplary User Device

Figure 5:
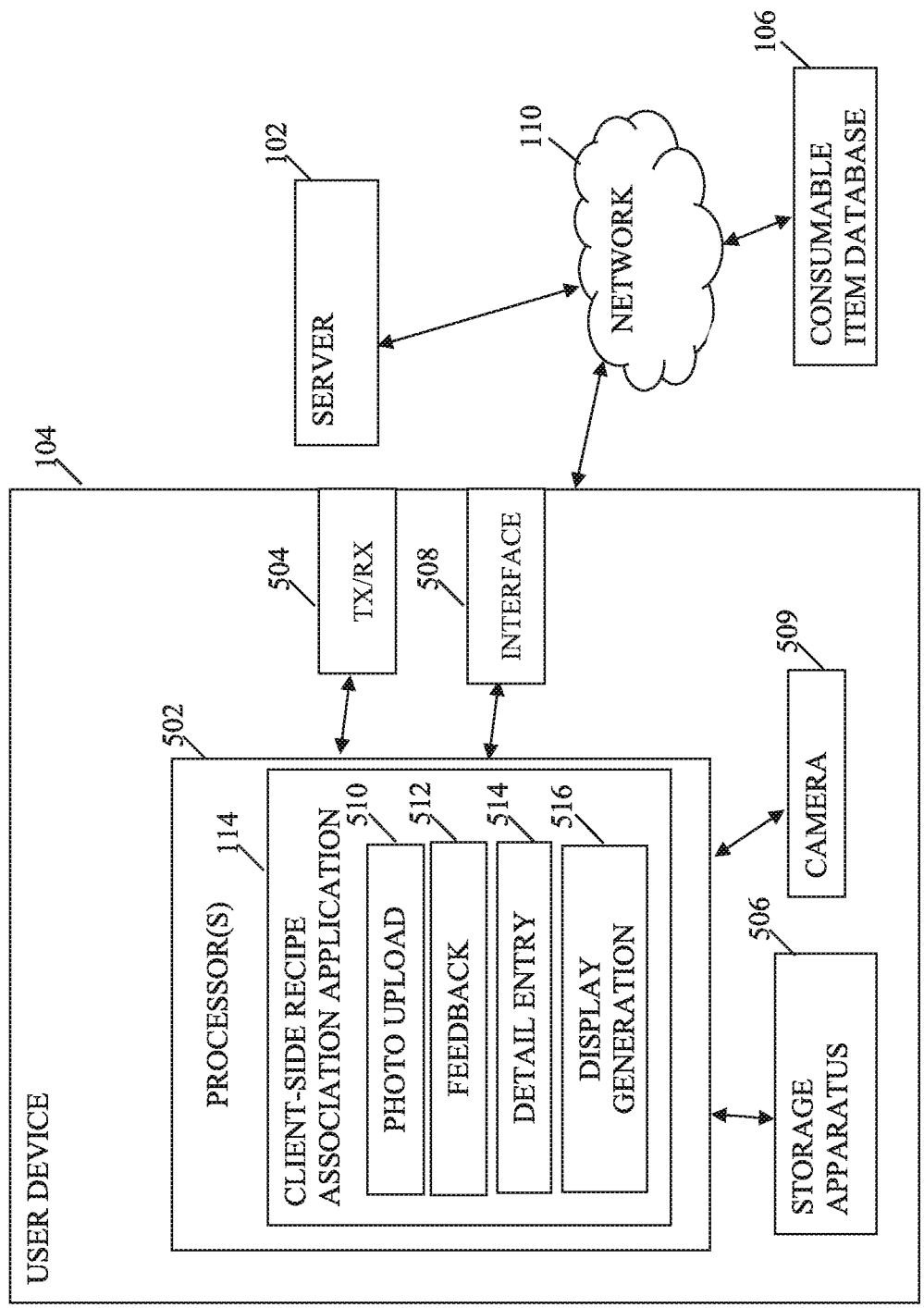
FIG. 5 is a block diagram illustrating an exemplary client device in accordance with one embodiment of the present disclosure.

Referring now to FIG. 5, an exemplary user device 104 is provided. The user device 104 may comprise a portable computerized device in one particular embodiment. As illustrated, the device 104 comprises a processor 502, a transceiver 504, a storage device 506, a user interface 508, and a camera 509. As discussed in further detail below, the processor 502 is operable to run at least a client-side recipe association application 114 thereon.

As noted above, the user device 104 may further comprise health-monitoring functionality. For example, the user device 104 may comprise a smart phone, smart watch, or other portable electronic device that is configured to both monitor user activity (such as via one or more sensors and/or inputs; not shown). Further, the user device 104 may be configured to access or run a computer application configured to enable a user to maintain a log of consumed items e.g., a nutrition monitoring application. The nutrition monitoring application may comprise a process in the client-side recipe association application 114 in at least one embodiment; or may comprise a separate application therefrom.

The transceiver 504 of the exemplary user device 104 illustrated in FIG. 5 enables receipt and transmission of communications to and from the user device 104. For example, the transceiver 504 facilitates the transmission of requests to match a recipe photograph and/or recipe details to existing recipes in the consumable item database 106 via a process running at the server 102 and facilitates the transmission of details regarding a consumable item log to a separate database in one embodiment. The transceiver 504 is also configured to receive data relating to recipe details to be added to a particular user's log received from e.g., the consumable item database directly 106 and/or provided via the server 102 application. As shown, communication is therefore enabled between the user device 104 and the server 102 and the consumable item database 106 as discussed herein.

The transceiver 504 may be any of various devices configured for communication with other electronic devices, including the ability to send communication signals and receive communication signals. The transceiver 504 may include different types of transceivers configured to communicate with different networks and systems. Such transceivers are well known and will be recognized by those of ordinary skill in the art. In some embodiments, the transceiver 504 includes at least one transceiver configured to allow the user device 104 to perform wireless communications with the cell towers of the wireless telephony network, as will be recognized by those of ordinary skill in the art. The wireless telephony network may comprise any of several known or future network types. For example, the wireless telephony network may comprise commonly used cellular phone networks using CDMA, GSM or FDMA communication schemes, as well as various other current or future wireless telecommunications arrangements. In some embodiments, the transceiver 504 includes at least one transceiver configured to allow the user device 104 to communicate with any of various local area networks using Wi-Fi, Bluetooth® or any of various other communications schemes.

The camera 509 of the user device 104 comprises a traditional camera as is well known in the art which may be integrated into the user device 104. The camera 509 is used in one embodiment to obtain a photograph of an image associated with a multi-ingredient consumable item (i.e., recipe). It is appreciated that the camera 509 may further be used to capture images of text such as an ingredient list or recipe title. In a further embodiment, the camera 509 may be used to capture an image of a bar code, universal product code (UPC), and/or QR code associated to a multi-ingredient consumable item.

The storage apparatus 506 of the exemplary user device 104 in FIG. 5 is configured to store photographs to be uploaded, user profile records, local copies of consumable item records which were logged by the user, a client-side version of the aforementioned computer applications (e.g., a nutrition monitoring application and/or the client-side recipe association application 114), and any other locally created or stored data. In another embodiment, one or more of the consumable item records which were logged by the user and/or user profile data are stored at a remote storage apparatus and/or database (such as the consumable item database 106 and/or a user profile database (not shown)).

In one embodiment the user interface 508 comprises a display configured to enable the user to receive information and make selections, enter data, etc. For example, the interface may comprise an interactive display such as a touch screen or the like.

The processor 502 is configured to execute at least a client-side recipe association application 114 thereon. The client-side recipe association application 114 may be downloaded via a network interface from a web-based server, or alternatively be pre-installed on the device 104 at purchase. The client-side recipe association application 114 comprises a plurality of instructions which are configured to, when executed by the processor 502, facilitate recipe capturing for nutrition logging by enabling a user to conveniently log food via uploading a recipe image. In one specific embodiment, the client-side recipe association application 114 comprises a plurality of functional applications including: a photograph upload application 510, a feedback application 512, a detail entry application 514, and a display generation application 516. Each of these will be discussed in turn below.

The photograph upload application 510 comprises a plurality of instructions which are configured to, when executed by the processor 502, enable the user to select a photograph to be uploaded in a query for a matching image among a database of consumable items. In one embodiment, the photograph upload application 510 is configured to access a camera roll (i.e., photographs in the storage apparatus 506 of the user device 104). Alternatively, the photograph upload application 510 may be configured to access a separate camera application which controls the camera 509 to facilitate taking a new photograph. As discussed in greater detail elsewhere herein, the user is able to select a photograph which accurately represents a recipe image (i.e., an image associated to a recipe such as in a cookbook, webpage, blog, etc.).

The feedback application 512 comprises a plurality of instructions which are configured to, when executed by the processor 502, enable the user to provide feedback relating to a list of one or more identified recipes. As discussed elsewhere herein, once the user uploads a photograph or other details relating to a recipe, the server 102 is configured to identify one or more entries in the consumable item database 106 which are a predetermined nearness to the image or details provided by the user (methods and systems for this identification will be discussed in greater detail elsewhere herein). The one or more identified entries are provided to the user via the user interface 508 and via the feedback application 512, the user may indicate which of these comprises the intended consumable item. Such feedback information is provided (via the transceiver 504) to the server 102 or other entity which is configured to use the feedback to make the selection of potentially matching consumable items more accurate in one embodiment (discussed elsewhere herein).

The detail entry application 514 comprises a plurality of instructions which are configured to, when executed by the processor 502, provide one or more GUI which enable the user to enter one or more details relating to a recipe. In one example, the user may be provided with options to select options from among a list, type details using a keyboard displayed on a display screen of the device 104 or integrated onto the device itself 104, and/or enter spoken details via a microphone of the device 104. Other means for capturing details may include that the detail entry application 514 is configured to include optical character recognition (OCR) capabilities, thus enabling the user to enter details via photographing the recipe itself. In yet another embodiment, the detail entry application 514 is configured to enable the user to scan or take a photograph of a bar code, QR code, or the like. The bar code, QR code or other is then used in a search to identify the recipe ingredients.

The display generation application 516 comprises a plurality of instructions which are configured to, when executed by the processor 502, enable the generation of a plurality of user interfaces or displays discussed herein. Specifically, one or more user interfaces may be generated which display the aforementioned potentially matching recipes, display the entered recipe details, display images associated with the potentially matching recipes and/or uploaded by the user, display various recipe detail collection pages, enable the user to interact with particular pages, and so forth.

It is appreciated that the user device 104 may comprise additional applications (now shown) which contribute to the functioning thereof as described herein and/or the foregoing functionality may be distributed across more applications or combined into fewer applications. For example, the aforementioned nutrition monitoring application may be provided via a separate application than the client-side recipe association application 114. These and other components of the user device 104 will be clear to a person of ordinary skill in the art given the discussion of the functionality herein.

In one embodiment, the aforementioned processing is performed via coordination of a distributed application having client and network-side components. The network-side component may be run at a network entity and the client-side component run at the user device 104.

It is appreciated that the user device 104 may comprise additional applications (now shown) which contribute to the functioning thereof as described herein and/or the foregoing functionality may be distributed across more applications or combined into fewer applications. These and other components of the user device 104 will be clear to a person of ordinary skill in the art given the discussion of the functionality herein.

The herein-described applications enable a user to efficiently enter recipe details by uploading a photograph of an image from the recipe which is matched (at a server 102) to a plurality of stored recipes entered by other users and include e.g., the client-side recipe association application 114, the photograph upload application 510, the feedback application 512, the detail entry application 514, and the display generation application 516. A permanent copy of the programming instructions for these applications (114, 510, 512, 514, and/or 516) may be placed into permanent storage devices (such as e.g., the storage apparatus 506) during manufacture of the user device 104, or in the field, through e.g., a distribution medium (not shown), such as a compact disc (CD), or from a distribution server (not shown) via the network 110. That is, one or more distribution media having an implementation of the agent program may be employed to distribute the agent and program various computing devices.

The herein described recipe association applications (114, 510, 512, 514, and/or 516) improve the functioning of the user device 104 by enabling it to provide a means for a user to upload a photograph from a recipe and receive at least one matching recipe. Furthermore, devices that are able to enable a user to efficiently identify and enter consumed items as disclosed herein can operate to more effectively enable nutrition logging for the identified recipe.

Exemplary Sever

Figure 6:
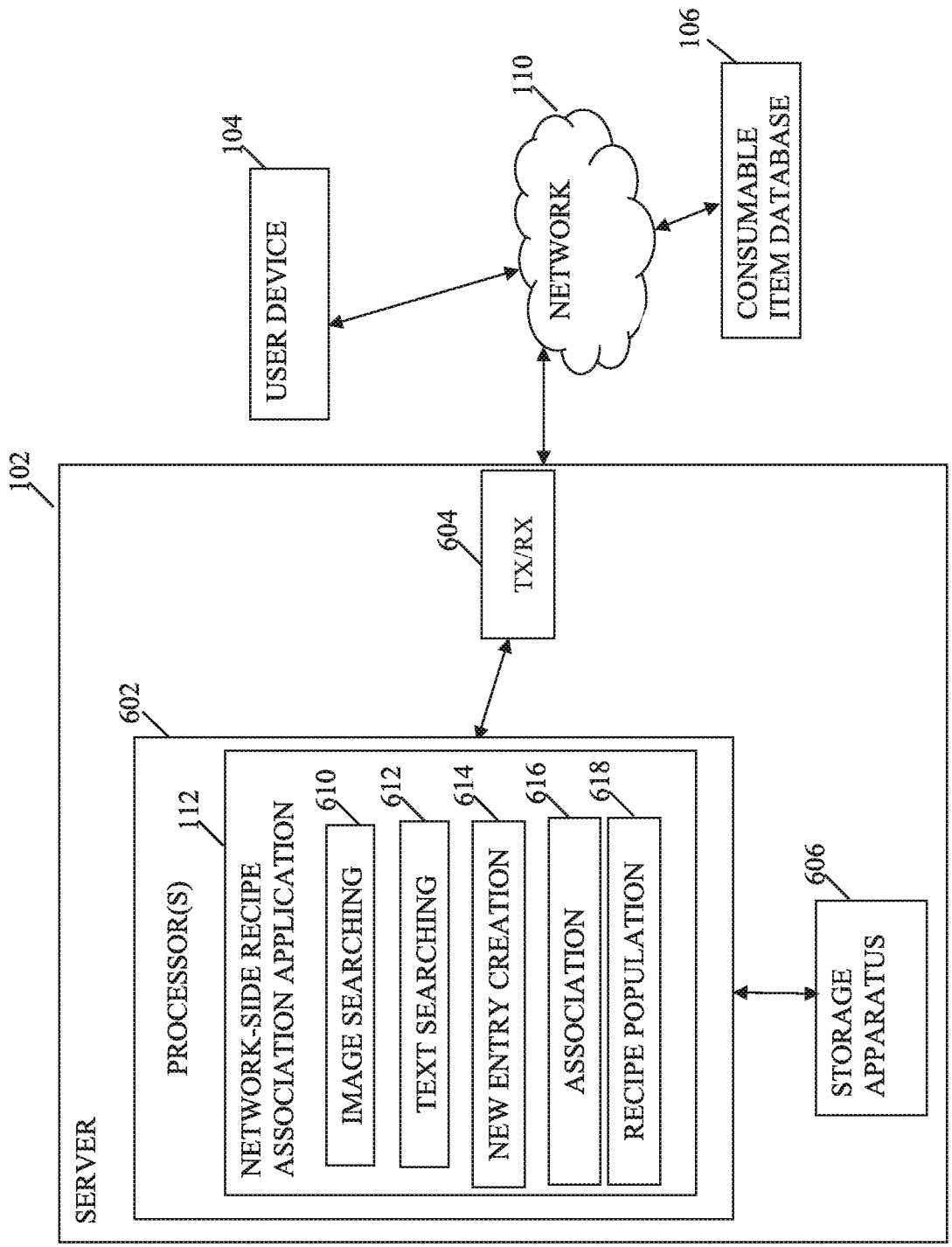
FIG. 6 is a block diagram illustrating an exemplary server apparatus in accordance with one embodiment of the present disclosure.

Referring now to FIG. 6, an exemplary server device 102 is provided. The server 102 may comprise a computerized device having a processor 602, a transceiver 604, and a storage device 606. As discussed in further detail below, the processor 602 is operable to run at least a network-side recipe association application 112 thereon.

The transceiver 604 of the exemplary server 102 illustrated in FIG. 6 enables receipt and transmission of communications to and from the server 102. For example, the transceiver 604 facilitates the receipt of queries (including uploaded photographs or other recipe details) from the user device 104; and the receipt of data records from the consumable item database 106. Additionally, the transceiver 604 facilitates transmission to the user devices 104 of the one or more consumable item records which are identified as potentially matching to the recipe details entered by the user.

The storage apparatus 606 of the exemplary server 102 in FIG. 6 is configured to store local copies of e.g., the applications run at the processor 602, local copies of lists of consumable records to be provided to the user device, local copies of uploaded images and/or recipe details, and/or any other locally created or stored data.

The processor 602 is configured to execute at least a network-side recipe association application 112 thereon. The network-side recipe association application 112 comprises a plurality of instructions which are configured to, when executed by the processor 602, facilitate the identification of one or more consumable item records which most closely match entered recipe details and/or a photograph of a recipe image. In one specific embodiment, the network-side recipe association application 112 comprises a plurality of functional applications including: an image searching application 610, a text searching application 612, a new entry creation application 614, an association application 616, and a recipe population application 618. Each of these will be discussed in turn below.

The image searching application 610 comprises a plurality of instructions which are configured to, when executed by the processor 602, enable the server 102 to obtain an image uploaded from the user and query the consumable item database 106 for one or more images which are sufficiently similar thereto. In one embodiment, the image searching application 610 may utilize deep convolutional neural network (CNN) techniques such as those discussed in A. Krizhevsky, I. Sutskever, and G. E. Hinton. *ImageNet Classification with Deep Convolutional Neural Networks. Advances in Neural Information Processing Systems* 25 (*NIPS* 2012) to classify images; as discussed elsewhere herein.

The text searching application 612 comprises a plurality of instructions which are configured to, when executed by the processor 602, enable the server 102 to obtain text provided by the user relating to the recipe details (such as a title for the recipe and/or ingredients) and query the consumable item database 106 for one or more records which are sufficiently similar thereto. The text searching application 612 may determine a match by comparing the text letter by letter, and/or by employing a text comparison means which takes into account spelling errors, synonyms, etc.

The new entry creation application 614, comprises a plurality of instructions which are configured to, when executed by the processor 602, cause the details of a user-entered recipe to be saved at the consumable item database 106 as a new entry. As noted above, a new entry is created when an existing item within the consumable database 106 which matches the user-entered details cannot be identified. In such cases, the user-entered details and image (where appropriate) are utilized by the new entry creation application 614 to populate a new data record. The new data record is then provided such as via the transceiver 604 to the consumable item database 106. The new data record and/or information relating thereto may also be provided back to the user device 104 for storage and/or nutrition logging thereat.

The association application 616 comprises a plurality of instructions which are configured to, when executed by the processor 602, cause a user-provided image and/or recipe details to be associated to an existing record in the consumable item database 106. In one embodiment, the association may comprise addition of the user-uploaded image to the identified record. In another embodiment, the association may comprise addition of the user-uploaded recipe details to the identified record. For example, a recipe creator may update the image associated to their recipe in a subsequent volume of a cookbook. Hence, the user-uploaded image may be slightly different from the image of the existing recipe in the consumable item database 106; thus the new image is also added to the record as being related to the same recipe. In this instance subsequent users who upload the original version of the image or the new version of the image will still both be directed to the same correct recipe. Similar logic may apply to the other user-entered details including e.g., title/name of the recipe, ingredients, etc.

The recipe population application 618 comprises a plurality of instructions which are configured to, when executed by the processor 602, enable a recipe being entered manually by a user to be automatically populated when it is determined that the desired recipe corresponds to an existing recipe in the database 106. In one embodiment, the existing recipe is identified via a back-ground search of the text entered by the user for the desired recipe (such as via the text searching application 612).

It is appreciated that the server 102 may comprise additional applications (now shown) which contribute to the functioning thereof as described herein and/or the foregoing functionality may be distributed across more applications or combined into fewer applications. These and other components of the server 102 will be clear to a person of ordinary skill in the art given the discussion of the functionality herein.

The herein-described applications enable data transformation topologies to be transported and/or distributed within a network of devices as discussed throughout the disclosure and include e.g., the network-side recipe association application 112, the image searching application 610, the text searching application 612, the new entry creation application 614, the association application 616, and the recipe population application 618. A permanent copy of the programming instructions for these applications (112, 610, 612, 614, 616, and/or 618) may be placed into permanent storage devices (such as e.g., the storage apparatus 606) during manufacture of the server 102, or in the field, through e.g., a distribution medium (not shown), such as a compact disc (CD), or from a distribution server (not shown) via the network 110. That is, one or more distribution media having an implementation of the agent program may be employed to distribute the agent and program various computing devices.

The herein-described applications (112, 610, 612, 614, 616, and/or 618) improve the functioning of the server 102 by enabling it to provide a means for a user to upload a photograph from a recipe and receive at least one matching recipe. Furthermore, devices that are able to enable a user to efficiently identify and enter consumed items as disclosed herein can operate to more effectively enable nutrition logging for the identified recipe.

Exemplary Image Matching Techniques

As noted above, the herein disclosed embodiments rely on an application at the server 102 (such as the network-side recipe association application 112) to identify one or more consumable item records which match the recipe the user seeks to enter (either by image upload or other recipe detail upload). The mechanisms by which the server is configured to identify a recipe in the consumable item database 106 having sufficient similarity to the user-entered recipe may include pattern recognition mechanisms, machine learning mechanisms, and/or deep learning mechanisms. The application of each of these will be discussed in further detail herein.

In one exemplary embodiment, an uploaded image (such as a photograph of an image associated to a multi-ingredient recipe) is compared to a plurality of images in a database (such as the consumable item database 106) via pattern recognition. The particular pattern recognition may include a set of "training data" to facilitate supervised learning over time, or alternatively may comprise "unsupervised learning". In either instance, pattern recognition techniques identify various features in the uploaded image which are matched to corresponding features in the database images. A match is determined when the images are determined to vary by no more than a predetermined threshold amount.

In another embodiment, machine learning techniques may be utilized to identify one or more matching consumable item record images to an uploaded image. It is noted that the objective of such machine learning techniques is to enable a computer system to generalize from its experience, i.e., to accurately place new data based on past experience. In one variant, the past experience may comprise learning from a set of training data, which the system uses to build a general model in order to produce sufficiently accurate new data classifications/decisions. Any number of the available machine learning approaches may be utilized by the herein-disclosed system. For example, the network-side recipe association application 112 running at the server 102 may be configured to employ decision tree learning, association rule learning, artificial neural networks, deep learning, inductive logic programming, support vector machines, clustering, Bayesian networks, reinforcement learning, representation learning, similarity and metric learning, sparse dictionary learning, and/or genetic algorithms.

Specifically, as used herein, deep learning and artificial neural networks have been used to identify images in the previously referenced *ImageNet Classification with Deep Convolutional Neural Networks. Advances in Neural Information Processing Systems* 25 (*NIPS* 2012) by A. Krizhevsky, I. Sutskever, and G. E. Hinton. As discussed therein, a large, deep convolutional neural network was used to classify 1.2 million high-resolution images. The network utilized comprises eight learned layers (five convolutional and three fully-connected); however, other arrangements may be utilized in the disclosure herein with equal or similar success.

In another embodiment, features similar to those discussed in e.g., A. Myers, N. Johnson, V. Rathod, A. Korattikara, A. Gorban, N. Silberman, S. Guadarrama, G. Papandreou, J. Huang, K. Murphy. *Im2Calories: towards an automated mobile vision food diary.* 2015 *IEEE International Conference on Computer Vision* (*ICCV*) may be utilized to enable identification of food items. As discussed therein, the system is configured to receive a photograph uploaded by a user taken of the user's meal. The component foods are identified from the photograph, and nutrition information may then be pulled from a database therefor. It is important to note, as a point of distinction, that the present disclosure, as noted above, focuses primarily on the identification of multi-ingredient consumable items from photographs taken of images provided in conjunction with the items, as opposed to images of the consumable items themselves. For example, images may be provided with a particular recipe (multi-ingredient consumable item), the user in the present disclosure photographs the recipe image and uploads this image for comparison.

The present disclosure may, however, similarly utilize a CNN-based classifier to efficiently identify a match between uploaded images and database images. Specifically, the present disclosure may rely on a commercially available CNN (such as e.g., the GoogLeNet CNN) which is modified so as to have its larger softmax replaced with a smaller one. Using the example of the GoogLeNet CNN, the 1000-way softmax may be replaced with a 101-way softmax in one specific example. Additionally, the dataset utilized will relate specifically in the present disclosure to the consumable item database 106 and/or the records contained therein (including single item records and multi-ingredient records). However, other arrangements and datasets may be utilized with equal success. Additionally, other pre-trained commercially available CNN's may also be utilized including e.g., AlexNet, VGG, etc.

It will be appreciated that variants of the above-described and other features and functions, or alternatives thereof, may be desirably combined into many other different systems, applications or methods. Various presently unforeseen or unanticipated alternatives, modifications, variations or improvements may be subsequently made by those skilled in the art that are also intended to be encompassed by the following claims.

It will be appreciated that the various ones of the foregoing aspects of the present disclosure, or any parts or functions thereof, may be implemented using hardware, software, firmware, tangible, and non-transitory computer readable or computer usable storage media having instructions stored thereon, or a combination thereof, and may be implemented in one or more computer systems.

It will be apparent to those skilled in the art that various modifications and variations can be made in the disclosed embodiments of the disclosed device and associated methods without departing from the spirit or scope of the disclosure. Thus, it is intended that the present disclosure covers the modifications and variations of the embodiments disclosed above provided that the modifications and variations come within the scope of any claims and their equivalents.

What is claimed is:

1. A method for enabling efficient association of a desired multi-ingredient consumable item to one of a plurality of multi-ingredient consumable item records in a database, individual ones of said plurality of multi-ingredient consumable item records being associated to a plurality of data and at least one image, respectively, said method comprising:

receiving at a server apparatus a photograph uploaded from a user device, said photograph comprising a photograph taken via a camera function of said user device of an image provided in association with a multi-ingredient consumable item;

searching said database for an image which matches to said image of said uploaded photograph;

when one of said individual ones of said plurality of multi-ingredient consumable item records is identified as being associated to said image which matches said uploaded photograph:

providing a portion of said data associated to said identified one of said individual ones of said plurality of multi-ingredient consumable item records to said user device;

receiving feedback from a user of said user device indicating whether said identified one of said individual ones of said plurality of multi-ingredient consumable items comprises said desired multi-ingredient consumable item; and when said feedback indicates that said one of said identified one of said individual ones of said plurality of multi-ingredient consumable item records corresponds to the desired multi-ingredient consumable item, providing a remaining portion of said data associated to said identified one of said individual ones of said plurality of multi-ingredient consumable item records to said user device for logging thereat; and when none of said individual ones of said plurality of multi-ingredient consumable item records is identified as being associated to said image, or when said feedback indicates that said one of said identified one of said individual ones of said plurality of multi-ingredient consumable item records does not correspond to the desired multi-ingredient consumable item, enabling said user to create a new consumable item record.

2. The method of claim 1, wherein said act of searching said database comprises using a convolutional neural network (CNN)-based classifier to efficiently identify said image which matches said uploaded photograph.

3. The method of claim 1, wherein said portion of said data comprises a title of said identified one of said individual ones of said plurality of multi-ingredient consumable item records presented in a list of titles each having some threshold level of similarity to said uploaded photograph.

4. The method of claim 1, wherein said remaining portion of said data comprises data relating to a number of servings, each ingredient in said multi-ingredient consumable item, and/or nutrition data.

5. The method of claim 1, further comprising providing said new consumable item record is for storage at said database.

6. The method of claim 1, further comprising providing said new consumable item record for logging at said user device.

7. The method of claim 1, wherein said new consumable item record comprises said uploaded photograph and a plurality of data relating thereto.

8. A non-transitory, computer readable medium comprising a plurality of instructions which are configured to, when executed, cause a server device to:
receive a photograph uploaded from a user device, said photograph comprising a photograph taken via a camera function of said user device of an image provided in association with a multi-ingredient consumable item;
search a database comprising a plurality of multi-ingredient consumable item records, individual ones of said records comprising a plurality of data and at least one image, said search comprising a search for an image which matches to said image of said uploaded photograph;
identify one of said individual ones of said plurality of multi-ingredient consumable item records as being associated to said image which matches said image of said uploaded photograph;
provide a portion of said data associated to said identified one of said individual ones of said plurality of multi-ingredient consumable item records to said user device; and
receive feedback from a user of said user device indicating whether said identified one of said individual ones of said plurality of multi-ingredient consumable items comprises a desired multi-ingredient consumable item; and
when said feedback indicates that said one of said identified one of said individual ones of said plurality of multi-ingredient consumable item records does not correspond to the desired multi-ingredient consumable item, said plurality of instructions are further configured to cause said server device to enable said user to create a new consumable item record comprising said uploaded photograph and a plurality of data relating thereto, said new consumable item record being provided for storage at said database.

9. The computer readable medium of claim 8, wherein when said feedback indicates that said one of said identified one of said individual ones of said plurality of multi-ingredient consumable item records corresponds to the desired multi-ingredient consumable item, said plurality of instructions are further configured to cause said server device to provide a remaining portion of said data associated to said identified one of said individual ones of said plurality of multi-ingredient consumable item records to said user device for logging thereat.

10. The computer readable medium of claim 9, wherein said plurality of instructions are further configured to cause said server device to enable said user to edit said remaining portion of said multi-ingredient consumable item record to create a new record, said new consumable item record being provided for storage at said database.

11. The computer readable medium of claim 8, wherein said search of said database comprises utilization of a convolutional neural network (CNN)-based classifier to efficiently identify said image which matches said uploaded photograph.

12. The computer readable medium of claim 11, wherein said CNN-based classifier comprises a modified GoogLeNet CNN, said modification comprising replacement of its softmax with a smaller softmax and utilization of said plurality of multi-ingredient consumable item records in said database.

13. A network apparatus configured to enable efficient association of a desired multi-ingredient consumable item to one of a plurality of multi-ingredient consumable item records in a database, individual ones of said plurality of multi-ingredient consumable item records being associated to a plurality of data and at least one image, respectively, said apparatus comprising:
one or more transceivers;
a storage apparatus; and
a processor configured to execute at least one computer application thereon, said computer application comprising a plurality of instructions which are configured to, when executed, cause said network apparatus to:
receive a photograph uploaded from a user device, said photograph comprising a photograph taken via a camera function of said user device of an image provided in association with a multi-ingredient consumable item;
search said database for an image which matches to said image of said uploaded photograph;
when one of said individual ones of said plurality of multi-ingredient consumable item records is identified as being associated to said image which matches said image of said uploaded photograph:
provide a portion of said data associated to said identified one of said individual ones of said plurality of multi-ingredient consumable item records to said user device; and
receive feedback from a user of said user device indicating whether said identified one of said individual ones of said plurality of multi-ingredient consumable items comprises said desired multi-ingredient consumable item.

14. The network apparatus of claim 13, wherein when said feedback indicates that said one of said identified one of said individual ones of said plurality of multi-ingredient consumable item records corresponds to the desired multi-ingredient consumable item, providing a remaining portion of said data associated to said identified one of said individual ones of said plurality of multi-ingredient consumable item records to said user device for logging thereat.

15. The network apparatus of claim 13, wherein when said feedback indicates that said one of said identified one of said individual ones of said plurality of multi-ingredient consumable item records does not correspond to the desired multi-ingredient consumable item, enabling said user to create a new consumable item record comprising said uploaded photograph and a plurality of data relating thereto, said new consumable item record being provided for storage at said database.

16. The network apparatus of claim 13, wherein said search of said database comprises a utilization of a convolutional neural network (CNN)-based classifier to efficiently identify said image which matches said uploaded photograph.

17. The network apparatus of claim 16, wherein said CNN-based classifier comprises a modified GoogLeNet CNN, said modification comprising replacement of its softmax with a smaller softmax and utilization of said plurality of multi-ingredient consumable item records in said database.

18. The network apparatus of claim 13, wherein said portion of said data comprises a title of said identified one of said individual ones of said plurality of multi-ingredient consumable item records presented in a list of titles each having some threshold level of similarity to said uploaded photograph.

* * * * *